United States Patent
Arisandy et al.

(10) Patent No.: US 9,200,242 B2
(45) Date of Patent: *Dec. 1, 2015

(54) THICKENER COMPRISING AT LEAST ONE CATIONIC POLYMER

(71) Applicant: BASF SE, Ludwigshafen (DE)

(72) Inventors: Christofer Arisandy, Ilvesheim (DE); Reinhold J. Leyrer, Dannstadt-Schauernheim (DE); Ouidad Benlahmar, Mannheim (DE)

(73) Assignee: BASF SE (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/670,833

(22) Filed: Nov. 7, 2012

(65) Prior Publication Data

US 2013/0121942 A1    May 16, 2013

Related U.S. Application Data

(60) Provisional application No. 61/558,444, filed on Nov. 11, 2011.

(51) Int. Cl.
| | | |
|---|---|---|
| *C11D 17/00* | (2006.01) | |
| *A61Q 5/02* | (2006.01) | |
| *A61Q 5/06* | (2006.01) | |
| *A61Q 19/10* | (2006.01) | |
| *A61Q 5/12* | (2006.01) | |
| *A61K 8/81* | (2006.01) | |
| *C08F 220/34* | (2006.01) | |
| *C11D 3/37* | (2006.01) | |
| *C08F 220/18* | (2006.01) | |
| *C08F 220/28* | (2006.01) | |

(52) U.S. Cl.
CPC ............ *C11D 17/003* (2013.01); *A61K 8/8152* (2013.01); *A61Q 5/02* (2013.01); *A61Q 5/06* (2013.01); *A61Q 5/12* (2013.01); *A61Q 19/10* (2013.01); *C08F 220/34* (2013.01); *C11D 3/3769* (2013.01); *A61K 2800/48* (2013.01); *A61K 2800/548* (2013.01); *A61K 2800/5426* (2013.01); *C08F 2220/1891* (2013.01); *C08F 2220/286* (2013.01)

(58) Field of Classification Search
None
See application file for complete search history.

(56) References Cited

U.S. PATENT DOCUMENTS

| | | | |
|---|---|---|---|
| 3,234,258 A | 2/1966 | Morris | |
| 5,075,041 A | 12/1991 | Lutz | |
| 5,916,967 A * | 6/1999 | Jones et al. | 524/732 |
| 6,020,304 A | 2/2000 | Ceulemans et al. | |
| 6,107,398 A | 8/2000 | Mallo et al. | |
| 2004/0258648 A1* | 12/2004 | Creamer et al. | 424/70.16 |
| 2006/0260071 A1 | 11/2006 | Legrand | |
| 2008/0312343 A1 | 12/2008 | Braun et al. | |
| 2009/0074692 A1 | 3/2009 | Biganska et al. | |
| 2011/0230387 A1 | 9/2011 | Leyrer et al. | |

FOREIGN PATENT DOCUMENTS

| | | |
|---|---|---|
| CA | 2053900 A1 | 10/1990 |
| EP | 172724 B1 | 7/1991 |
| EP | 172025 B1 | 10/1991 |
| EP | 172723 B2 | 11/1997 |
| EP | 343840 B2 | 7/2002 |
| WO | WO-90/13533 A1 | 11/1990 |
| WO | WO-95/07331 A1 | 3/1995 |
| WO | WO-03/102043 A1 | 12/2003 |
| WO | WO-2005097834 A3 | 3/2006 |
| WO | WO-2009019225 A3 | 5/2009 |
| WO | WO-2010078959 A1 | 7/2010 |
| WO | WO-2010079100 A1 | 7/2010 |

OTHER PUBLICATIONS

Moraes RP et al. "Evaluation of alternative comonomers for the production of ASE and HASE thickeners", J Colloid Interface Sci. Dec. 1, 2010;352(1):19-29. doi: 10.1016/j.jcis.2010.08.038. Epub Aug. 16, 2010.*

Karlson, "Hydrophobically modified polymers rtheology and molecular associations", pp. 1-132 (Oct. 4, 2002).*

* cited by examiner

*Primary Examiner* — Ernst V Arnold
*Assistant Examiner* — Kyung Sook Chang
(74) *Attorney, Agent, or Firm* — Drinker Biddle & Reath LLP

(57) ABSTRACT

The present invention relates to a thickener comprising at least one cationic polymer and at least one activator. The at least one cationic polymer is preparable by polymerization of a) at least one water-soluble ethylenically unsaturated monomer comprising at least one cationic monomer, optionally at least one anionic monomer and/or optionally at least one nonionic monomer, b) at least one ethylenically unsaturated associative monomer, c) optionally at least one crosslinker, and d) optionally at least one chain transfer agent. The ratio of activator to cationic polymer is >10 to 100 [% by weight/% by weight].

29 Claims, No Drawings

THICKENER COMPRISING AT LEAST ONE CATIONIC POLYMER

This patent application claims the benefit of U.S. provisional application Ser. No. 61/558,444 filed on Nov. 11, 2011, incorporated in its entirety herein by reference.

The present invention relates to a thickener comprising at least one cationic polymer and at least one activator, wherein the ratio of activator to cationic polymer is >10:100 [% by weight/% by weight]. The cationic polymer is preparable by polymerization of at least one water-soluble, ethylenically unsaturated monomer and at least one ethylenically unsaturated associative monomer. The present invention further relates to a process for preparing the inventive thickener and to surfactant-containing formulations comprising at least one thickener. The invention further provides for the use of the surfactant-containing formulations, for example as a softener or as a liquid washing composition, and to the use of the thickener, for example as a viscosity modifier.

WO 03/102043 relates to aqueous formulations comprising a cationic polymer prepared from (i) a water-soluble, ethylenically unsaturated monomer or a monomer mixture comprising at least one cationic monomer, (ii) at least one crosslinker in an amount of more than 50 ppm based on component (i), and (iii) at least one chain transfer agent. The aqueous formulations can be used as thickeners in domestic formulations.

WO 2009/019225 relates to an aqueous dispersion of an alkali-soluble copolymer, said dispersion being suitable as an associative thickener. The copolymer comprises polymerized units of a) at least one ethylenically unsaturated carboxylic acid, b) at least one nonionic ethylenically unsaturated surfactant monomer, c) at least one $C_1$-$C_2$-alkyl methacrylate and d) at least one $C_2$-$C_4$-alkyl acrylate, where the alkyl chain length averaged over the number of alkyl groups of the alkyl acrylate is 2.1 to 4.0. The associative thickeners can be prepared by emulsion polymerization. The associative thickeners are suitable for use in washing and cleaning compositions.

Liquid Dispersion Polymer (LDP) compositions are disclosed in WO 2005/097834. These LDP compositions comprise a hydrophilic, water-soluble or swellable polymer with a neutralization content of about 25 to about 100%, a non-aqueous carrier phase and an oil-in-water surfactant. The hydrophilic, water-soluble or swellable polymer is preferably obtained by polymerization, for example of acrylic acid or methacrylic acid. The LDP dispersions are suitable for production of microparticulate thickeners, as used, for example, in aqueous or organic compositions, especially in personal care or pharmaceutical formulations.

WO 2010/078959 relates to cationic polymer thickeners consisting of a crosslinked water-swellable cationic polymer comprising at least one cationic monomer and optionally nonionic or anionic monomers, said polymer comprising less than 25% of water-soluble polymer chains, based on the total weight of the polymer. The polymer also comprises a crosslinker in a concentration of 500 to 5000 ppm relative to the polymer. The cationic polymer is prepared by inverse emulsion polymerization.

WO 2010/079100 discloses fabric softener compositions comprising polymers according to WO 2010/078959.

US 2008/0312343 relates to inverse latex compositions and to the use thereof as a thickener, and/or emulsifier, for example for production of cosmetic or pharmaceutical formulations. The inverse latex compositions comprise at least 50 to 80% by weight of at least one linear, branched or crosslinked organic polymer (P), at least 5 to 10% by weight of a water-in-oil-type emulsifier system, 5 to 45% by weight of at least one oil and up to 5% water. The polymer P comprises uncharged monomers and optionally cationic or anionic monomers. The inverse latex composition may optionally comprise up to 5% by weight of an oil-in-water-type emulsifier system. The inverse latex compositions can be prepared by inverse emulsion polymerization.

EP-A 172 025 relates to a dispersion in a continuous liquid phase of a polymer, which is formed by polymerization of an ethylenically unsaturated monomer comprising a hydrophobic group of at least eight carbon atoms and an ethylenically unsaturated monomer copolymerizable therewith. The dispersion is stable and essentially anhydrous, and comprises at least 40% by weight of polymer. In the polymerization, the copolymerizable, ethylenically unsaturated monomers used may, for example, be anionic monomers. The polymerization can be performed as an inverse emulsion polymerization.

EP-A 172 724 relates to polymers which are prepared by copolymerization of a) an ethylenically unsaturated monomer comprising a hydrophobic group with at least eight carbon atoms and b) water-soluble ethylenically unsaturated monomers. All monomers are soluble as a mixture in water, and the polymer is prepared by inverse emulsion polymerization. The polymer particles have a dry size of <4 µm. The monomer components b) used may be anionic monomers such as acrylic acid in the form of the free acid or as a water-soluble salt, and nonionic monomers such as acrylamide.

EP-A 172 723 relates to a process for flocculating a suspension using a water-soluble, essentially linear polymer with a "single point intrinsic viscosity" of >3. The polymer is a copolymer of two or more ethylenically unsaturated monomers comprising at least 0.5% by weight of a monomer, comprising hydrophobic groups. The polymer may also be a cationic polymer.

The problem underlying the present invention consists in the provision of novel thickeners. The object is achieved by the inventive thickeners comprising i) at least one cationic polymer preparable by polymerization of a) at least one water-soluble ethylenically unsaturated monomer comprising at least one cationic monomer, optionally at least one anionic monomer and/or optionally at least one nonionic monomer, b) at least one ethylenically unsaturated associative monomer, c) optionally at least one crosslinker, d) optionally at least one chain transfer agent, ii) at least one activator, where the ratio of activator to cationic polymer is >10 to 100 [% by weight/% by weight].

The inventive thickeners are notable in that they possess advantageous properties with regard to deposition, shear dilution, stabilization and/or viscosity (thickening). Deposition is understood to mean the deposition of the active ingredients of, for example, a fabric softener on a fiber during a washing operation. Applied to the present invention, this means that, for example, an inventive thickener comprising at least one cationic polymer (active ingredient) is present in a fabric softener and the fabric softener is used during or after the washing operation. The inventive thickeners promote this deposition of the active ingredient during or after the washing operation to a considerable degree. Particularly good properties with regard to deposition can be achieved when cationic polymers based on at least one associative monomer, a cationic monomer and a nonionic monomer such as acrylamide are used.

In the assessment of shear dilution, it is important that the thickener or the corresponding fabric softener, in its ground state, is viscous and thick, while it is thin in the course of stirring. The improved shear dilution has a positive effect on the lifetime and properties of pumps in the production of the fabric softener, promotes convenient dosage for the consumer and promotes the residue-free use of the fabric softener, especially in the washing machines which possess an automatic dosage device. The inventive thickeners increase the stability of the thickener per se and that of the corresponding formulation. The settling or creaming of particles is effectively prevented, irrespective of whether they are within the order of magnitude of nanometers, micrometers or millimeters. This is contributed to by the advantageous yield point of the inventive thickeners. They also have the advantage that any redispersion required and thickening are achieved very rapidly.

Inventive thickeners in which a mixture of at least two activators is present, at least one activator having a high HLB value and at least one activator having a low HLB value, are associated with an additional advantage. The combination of such an activator mixture with cationic polymers comprising at least one ethylenically unsaturated associative monomer unit leads to spontaneous phase inversion (within seconds) in the case of dilution of a thickener with water, without any requirement for additional energy input, for example in the form of stirring.

Another advantage in the case of the inventive thickeners is that the ratio of associative monomer to the overall polymer is relatively low. In the case of use of the thickener in surfactant-containing formulations, the effect of the associative monomers is optimal even in amounts of approx. 0.5% by weight (based on the polymer).

When the inventive thickeners are prepared by inverse emulsion polymerization in which the temperature is kept constant at at least 40° C., good uniformity of distribution of the associative monomer units in the cationic polymer can be observed. Especially in the case of small use amounts of, for example, 0.1 to 1% by weight of associative monomers, this is advantageous with regard to the overall abovementioned rheological properties such as thickening, shear dilution, stabilization, and washing and rinse effects.

Embodiments of the present invention in which the cationic polymers present in the thickener are prepared using little or no crosslinker are likewise associated with advantages. Due to the relatively high (water-)soluble components of the polymer, recoiling during a washing operation is reduced. Consequently, the article to be washed, even after repeated washing operations, has clean fibers which have been free effectively of soil particles, such that no graying is detected. Only very slight, if any, adhesion or redistribution of soil particles/polymers on the washed articles is observed.

A further advantage of the inventive thickeners, in which the cationic polymer is obtained by inverse emulsion polymerization at constant temperature, is manifested in surfactant-containing formulations, especially in surfactant-containing acidic formulations, because a high thickening performance and/or marked shear dilution are achieved in these formulations even at low thickener concentrations (<1% by weight).

In the context of the present invention, the definitions such as $C_1$-$C_{30}$-alkyl, as defined, for example, below for the $R_4$ radical in formula (II), mean that this substituent (radical) is an alkyl radical having a carbon atom number from 1 to 30. The alkyl radical may be either linear or branched and optionally cyclic. Alkyl radicals which have both a cyclic and a linear component are likewise covered by this definition. The same also applies to other alkyl radicals, for example a $C_1$-$C_4$-alkyl radical or a $C_{16}$-$C_{22}$-alkyl radical. The alkyl radicals may optionally also be mono- or polysubstituted by functional groups such as amino, quaternary ammonium, hydroxyl, halogen, aryl or heteroaryl. Unless stated otherwise, the alkyl radicals preferably do not have any functional groups as substituents. Examples of alkyl radicals are methyl, ethyl, n-propyl, isopropyl, n-butyl, isobutyl, 2-ethylhexyl, tert-butyl (tert-Bu/t-Bu), cyclohexyl, octyl, stearyl or behenyl.

The present invention is specified further hereinafter.

The inventive thickener comprises, as component i), at least one cationic polymer. The cationic polymer is preparable by polymerization of the following components a) and b), and optionally c) and d).

The component a) used is at least one water-soluble, ethylenically unsaturated monomer comprising at least one cationic monomer, optionally at least one anionic monomer and/or optionally at least one nonionic monomer. Cationic monomers as such, any anionic monomers present as such, and any nonionic monomers present as such are known to those skilled in the art.

The cationic monomer according to component a) is preferably selected from a compound of the formula (II)

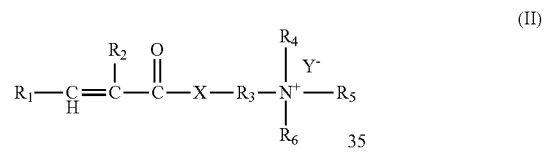

where
$R_1$ is H or $C_1$-$C_4$-alkyl,
$R_2$ is H or methyl,
$R_3$ is $C_1$-$C_4$-alkyl,
$R_4$, $R_5$ and $R_6$ are each independently H or $C_1$-$C_{30}$-alkyl,
X is —O— or —NH— and
Y is Cl; Br; I; hydrogensulfate or methosulfate.

Particularly preferred cationic monomers are 2-trimethylammonioethyl acrylate chloride (TMAEC) or 2-trimethylammonioethyl methacrylate chloride (TMAEMC). TMAEC is also referred to as quaternized dimethylaminoethyl acrylate (DMAEA, MeClq) and TMAEMC as quaternized dimethylaminoethyl methacrylate (DMAEMA, MeClq).

In one embodiment of the present invention, it is preferred that, in the cationic monomer of the formula (II),
i) $R_1$ and $R_2$ are each H or
ii) $R_1$ is H and $R_2$ is $CH_3$.

Any anionic monomer present in component a) is preferably selected from acrylic acid, methacrylic acid, itaconic acid, maleic acid or a salt thereof; the anionic monomer is especially sodium acrylate. When component a) comprises at least one anionic monomer, it is present (based on component a)) preferably to an extent of 0.5 to 20% by weight.

Component a) may optionally comprise at least one nonionic monomer. Apart from the nitrogen-containing monomers described below, for example the compounds of the formula (III), esters of the above-described anionic monomers are also suitable as nonionic monomers. Such nonionic monomers are preferably the methyl or ethyl esters of acrylic acid or methacrylic acid, such as ethyl acrylate or methyl acrylate. Additionally preferred are the corresponding dimethylamino-substituted esters such as dimethylaminoethyl (meth)acrylate.

Preferably, the nonionic monomer according to component a) in the cationic polymer is selected from N-vinylpyrrolidone, N-vinylimidazole, or a compound of the formula (III)

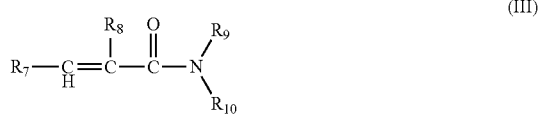

where
R$_7$ is H or C$_1$-C$_4$-alkyl,
R$_8$ is H or methyl, and
R$_9$ and R$_{10}$ are each independently H or C$_1$-C$_{30}$-alkyl,
The nonionic monomer is more preferably acrylamide, methacrylamide or dialkylaminoacrylamide. When component a) comprises at least one nonionic monomer, it is preferably present to an extent of 0.5 to 70% by weight.

In a preferred embodiment of the present invention, component a) in the cationic polymer comprises 30 to 99.5% by weight of at least one cationic monomer and 0.5 to 70% by weight of at least one nonionic monomer. In a further preferred embodiment of the present invention, component a) comprises 100% by weight of at least one cationic monomer.

Component b) used in the polymerization to prepare the cationic polymer is at least one ethylenically unsaturated associative monomer. Associative monomers as such are known to those skilled in the art. Suitable associative monomers are described, for example, in WO 2009/019225. Associative monomers are also described as surfactant monomers.

Preferably, the ethylenically unsaturated associative monomer according to component b) in the cationic polymer is selected from a compound of the formula (I)

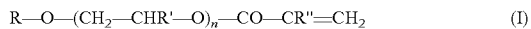

R—O—(CH$_2$—CHR'—O)$_n$—CO—CR"=CH$_2$ (I)

where
R is C$_6$-C$_{50}$-alkyl, preferably C$_8$-C$_{30}$-alkyl, especially C$_{16}$-C$_{22}$-alkyl,
R' is H or C$_1$-C$_4$-alkyl, preferably H,
R" is H or methyl,
n is an integer from 0 to 100, preferably 3 to 50, especially 25.

More preferably, component b) used is a compound of the formula (I) in which
R is C$_{16}$-C$_{22}$-alkyl,
R' is H,
R" is H or methyl and
n is 25.

Compounds of the formula (I) are commercially available in solution, for example under the Plex 6954 O name from Evonik Röhm GmbH. These are methacrylates of fatty alcohol ethoxylates. A suitable fatty alcohol ethoxylate is, for example, the commercially available Lutensol® AT 25 (BASF SE, Ludwigshafen, Germany).

The R radical in the compounds of the formula (I) may also be present as a mixture of radicals with different chain lengths, such as C$_{16}$ and C$_{18}$. One example thereof is C$_{16}$-C$_{18}$-fatty alcohol-(ethylene glycol)$_{25}$-ether methacrylate, where both C$_{16}$ and C$_{18}$ fatty alcohol radicals (in non-negligible amounts) are present as a mixture. In contrast, for example, in the compounds (of the formula (I)) behenyl-25 methacrylate and cetyl-25 methacrylate, the particular R radical is not present as a mixture but as a C$_{22}$ or C$_{16}$ chain. Other chain lengths occur only in the form of impurities. The number "25" in these compounds of the formula (I) represents the size of the variables n.

In the preparation of the cationic polymer by polymerization, at least one crosslinker may optionally be present as component c). Suitable crosslinkers are known to those skilled in the art. Preferably, the crosslinker according to component c) in the cationic polymer is selected from divinylbenzene; tetraallylammonium chloride; allyl acrylates; allyl methacrylates; diacrylates and dimethacrylates of glycols or polyglycols; butadiene; 1,7-octadiene, allylacrylamides or allylmethacrylamides; bisacrylamido acetic acid; N,N'-methylenebisacrylamide, or polyol polyallyl ethers such as polyallyl sucrose or pentaerythritol triallyl ether. Additionally suitable as a preferred crosslinker is dialkyldimethylammonium chloride.

It is additionally possible, in the preparation of the cationic polymer by polymerization, to use at least one chain transfer agent as component d). Suitable chain transfer agents are known to those skilled in the art. Preferred chain transfer agents according to component d) are selected from mercaptan, lactic acid, formic acid, isopropanol or hypophosphites.

Suitable polymerization processes for preparation of the cationic polymer or the inventive thickener comprising at least one cationic polymer, and any additives or assistants used in the polymerization or the thickener preparation process, are defined in detail in the text below.

Preferably, the inventive thickener comprises at least one cationic polymer preparable by polymerization of
a) 20 to 99.99% by weight, preferably 95 to 99.95% by weight (based on the polymer), of at least one water-soluble ethylenically unsaturated monomer comprising at least one cationic monomer, and optionally at least one anionic monomer and/or at least one nonionic monomer,
b) 0.01 to 80% by weight, preferably 0.05 to 5% by weight, more preferably 0.1 to 1% by weight (based on the polymer), of at least one ethylenically unsaturated associative monomer,
c) 0 to 0.3% by weight, preferably 0.01 to 0.1% by weight (based on the polymer), of optionally at least one crosslinker,
d) 0 to 0.3% by weight, preferably 0.01 to 0.1% by weight (based on the polymer), of optionally at least one chain transfer agent.

In a further embodiment of the present invention, the water-soluble components of the cationic polymer are more than 25% by weight (based on the total weight of the cationic polymer), especially when little or no crosslinker is used in addition to the associative monomer. Preferably more than 40% by weight, especially 70 to 100% by weight, of the cationic polymer is soluble in water. The solubility of the cationic polymer is determined by methods known to those skilled in the art, by admixing the cationic polymer present in the inventive thickener with a defined amount of water (see, for example, EP-A 343 840 or preferably the determination method of the sedimentation coefficient in the unit of svedberg (sved) according to P. Schuck, 'Size-distribution analysis of macromolecules by sedimentation velocity ultracentrifugation and Lamm equation modeling', Biophysical Journal 78, (3) (2000), 1606-1619).

Preferably, in this embodiment, the proportion of crosslinker (component c)) used in the polymerization of the cationic polymer is <1% by weight (based on the total amount of components a) to d)). More preferably, no crosslinker is used in the polymerization of the cationic polymer.

The inventive thickener further comprises, as components ii), at least one activator. Activators as such are known in principle to those skilled in the art.

Suitable activators are preferably surfactants, for example anionic, nonionic, cationic and/or amphoteric surfactants, which are disclosed, for example, in WO 2009/019225. Preference is given to using anionic and/or nonionic surfactants.

The nonionic surfactants used are preferably fatty alcohol alkoxylates. Fatty alcohol alkoxylates are also referred to as polyalkylene glycol ethers. Preferred fatty alcohol alkoxylates are alkoxylated, advantageously ethoxylated, especially primary alcohols having preferably 8 to 18 carbon atoms and an average of 1 to 12 mol of ethylene oxide (EO) per mole of alcohol, in which the alcohol radical may be linear or branched, preferably 2-methyl-branched, or may comprise linear and methyl-branched radicals in a mixture, as typically present in oxoalcohol radicals. Especially preferred are, however, alcohol ethoxylates with linear radicals formed from alcohols of native or technical origin with 12 to 18 carton atoms, for example formed from coconut alcohol, palm alcohol, tallow fat alcohol or oleyl alcohol—or mixtures as derivable, for example, from castor oil—and an average of 2 to 8 EO per mole of alcohol. The preferred ethoxylated alcohols include, for example, $C_{12}$-$C_{14}$-alcohols with 3 EO, 4 EO or 7 EO, $C_9$-$C_{11}$-alcohol with 7 EO, $C_{13}$-$C_{15}$-alcohols with 3 EO, 5 EO, 7 EO or 8 EO, $C_{12}$-$C_{18}$-alcohols with 3 EO, 5 EO or 7 EO and mixtures thereof such as mixtures of $C_{12}$-$C_{14}$-alcohol with 3 EO and $C_{12}$-$C_{18}$-alcohol with 7 EO. The degrees of ethoxylation reported are statistical averages which may be an integer or a fraction for a specific product. Preferred alcohol ethoxylates have a narrow homolog distribution (narrow range ethoxylates, NRE). In addition to these nonionic surfactants, it is also possible to use fatty alcohols with more than 12 EO. Examples thereof are tallow fat alcohol with 14 EO, 25 EO, 30 EO or 40 EO. It is also possible to use nonionic surfactants comprising EO and PO groups together in a molecule. In this context, it is possible to use block copolymers with EO-PO block units or PO-EO block units, but also EO-PO-EO copolymers or PO-EO-PO copolymers. It will be appreciated that it is also possible to use mixed-alkoxylation nonionic surfactants in which EO and PO units are not present in blocks but in random distribution. Such products are obtainable by simultaneous action of ethylene oxide and propylene oxide on fatty alcohols.

In addition, further nonionic surfactants used may also be alkyl glycosides or alkyl polyglycosides. Alkyl glycosides or alkyl polyglycosides are generally understood by the person skilled in the art to mean compounds composed of at least one alkyl fragment and at least one sugar or polysugar fragment. The alkyl fragments preferably derive from fatty alcohols having a carbon atom number of 12 to 22, and the sugar fractions preferably from glucose, sucrose or sorbitan.

For example, it is possible to use alkyl glycosides of the general formula (1)

$$R^1O(G)_x \tag{1}$$

in which $R^1$ is a primary straight-chain or methyl-branched, especially 2-methyl-branched, aliphatic radical having 8 to 22 and preferably 12 to 18 carbon atoms, and G is a glycoside unit having 5 or 6 carbon atoms, preferably glucose. The degree of oligomerization x, which specifies the distribution of monoglycosides and oligoglycosides, is any number between 1 and 10; x is preferably 1.2 to 1.4.

A further class of nonionic surfactants used with preference, which are used either as the sole nonionic surfactant or in combination with other nonionic surfactants, is that of alkoxylated, preferably ethoxylated or ethoxylated and propoxylated, fatty acid alkyl esters, preferably having 1 to 4 carbon atoms in the alkyl chain, especially fatty acid methyl esters, as described, for example, in Japanese patent application JP 58/217598, or which are preferably prepared by the process described in international patent application WO-A-90/13533.

Nonionic surfactants of the amine oxide type may also be suitable, for example N-cocoalkyl-N,N-dimethylamine oxide and N-tallowalkyl-N,N-dihydroxyethylamine oxide, and of the fatty acid alkanolamide type. The amount of these nonionic surfactants is preferably not more than that of the ethoxylated fatty alcohols, especially not more than half thereof.

Further suitable surfactants are polyhydroxy fatty acid amides of the formula (2),

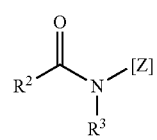

(2)

in which $R^2C(=O)$ is an aliphatic acyl radical having 6 to 22 carbon atoms, $R^3$ is hydrogen, an alkyl or hydroxyalkyl radical having 1 to 4 carbon atoms, and [Z] is a linear or branched polyhydroxyalkyl radical having 3 to 10 carbon atoms and 3 to 10 hydroxyl groups. The polyhydroxy fatty acid amides are known substances, which can be obtained typically by reductive amination of a reducing sugar with ammonia, an alkylamine or an alkanolamine, and subsequent acylation with a fatty acid, a fatty acid alkyl ester or a fatty acid chloride.

The group of the polyhydroxy fatty acid amides also includes compounds of the formula (3)

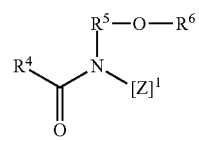

(3)

in which $R^4$ is a linear or branched alkyl or alkenyl radical having 7 to 12 carbon atoms, $R^5$ is a linear, branched or cyclic alkylene radical having 2 to 8 carbon atoms or an arylene radical having 6 to 8 carbon atoms, and $R^6$ is a linear, branched or cyclic alkyl radical or an aryl radical, or an oxyalkyl radical having 1 to 8 carbon atoms, preference being given to $C_1$-$C_4$-alkyl or phenyl radicals, and $[Z]^1$ is a linear polyhydroxyalkyl radical whose alkyl chain is substituted by at least two hydroxyl groups, or alkoxylated, preferably ethoxylated or propoxylated, derivatives of this radical. $[Z]^1$ is preferably obtained by reductive amination of a sugar, for example glucose, fructose, maltose, lactose, galactose, mannose or xylose. The N-alkoxy- or N-aryloxy-substituted compounds can then be converted to the desired polyhydroxy fatty acid amides, for example, according to WO-A-95/07331 by reaction with fatty acid methyl esters in the presence of an alkoxide as a catalyst.

The anionic surfactants used are, for example, those of the sulfonate and sulfate type. Useful surfactants of the sulfonate type include alkylbenzenesulfonates, preferably $C_9$-$C_{13}$-alkylbenzenesulfonates, olefinsulfonates, i.e. mixtures of alkene- and hydroxyalkanesulfonates, and disulfonates as obtained, for example, from $C_{12}$-$C_{18}$-monoolefins with terminal or internal double bonds by sulfonation with gaseous sulfur trioxide and subsequent alkaline or acidic hydrolysis of the sulfonation products. Also suitable are alkanesulfonates, preferably secondary alkanesulfonates, which are obtained, for example, from $C_{12}$-$C_{18}$-alkanes by sulfochlorination or sulfoxidation with subsequent hydrolysis or neutralization. Equally suitable are also the esters of α-sulfone fatty acids (ester sulfonates), for example the α-sulfonated methyl esters of hydrogenated coconut fatty acids, palm kernel fatty acids or tallow fatty acids.

Further suitable anionic surfactants are sulfonated fatty acid glyceryl esters. Fatty acid glyceryl esters are understood to mean the mono-, di- and triesters, and mixtures thereof as obtained in the preparation by esterification of a monoglycerol with 1 to 3 mol of fatty acid or in the transesterification of triglycerides with 0.3 to 2 mol of glycerol. Preferred sulfonated fatty acid glyceryl esters are the sulfonation products of saturated fatty acids having 6 to 22 carbon atoms, for example of caproic acid, caprylic acid, capric acid, myristic acid, lauric acid, palmitic acid, stearic acid or behenic acid.

Further suitable anionic surfactants are fatty alcohol sulfates, for example alk(en)yl sulfates. Preferred alk(en)yl sulfates are the alkali metal and especially the sodium salts of the sulfuric monoesters of the $C_{12}$-$C_{18}$ fatty alcohols, for example of coconut fatty alcohol, tallow fatty alcohol, lauryl alcohol, myristyl alcohol, cetyl alcohol or stearyl alcohol, or of the $C_{10}$-$C_{20}$ oxo alcohols and those monoesters of secondary alcohols of these chain lengths. Additionally preferred are alk(en)yl sulfates of the chain length mentioned which comprise a synthetic straight-chain alkyl radical produced on a petrochemical basis, which have analogous degradation behavior to the equivalent compounds based on fatty-chemical raw materials. In the interests of washing technology, preference is given to the $C_{12}$-$C_{16}$-alkyl sulfates and $C_{12}$-$C_{15}$-alkyl sulfates, and also $C_{14}$-$C_{15}$-alkyl sulfates. Suitable anionic surfactants are also 2,3-alkyl sulfates, which are prepared, for example, according to U.S. Pat. No. 3,234,258 or U.S. Pat. No. 5,075,041 and can be obtained as commercial products from Shell Oil Company under the DAN® name.

Also suitable are the sulfuric monoesters of the straight-chain or branched $C_7$-$C_{21}$-alcohols ethoxylated with 1 to 6 mol of ethylene oxide, such as 2-methyl-branched $C_7$-$C_{11}$ alcohols with an average of 3.5 mol of ethylene oxide (EO) or $C_{12}$-$C_{18}$-fatty alcohols with 1 to 4 EO.

Further suitable anionic surfactants are also the salts of alkylsulfosuccinic acid, which are also referred to as sulfosuccinates or as sulfosuccinic esters, and which are monoesters and/or diesters of sulfosuccinic acid with alcohols, preferably fatty alcohols and especially ethoxylated fatty alcohols. Preferred sulfosuccinates comprise $C_8$-$C_{18}$-fatty alcohol radicals or mixtures thereof. Especially preferred sulfosuccinates comprise a fatty alcohol radical which derives from ethoxylated fatty alcohols. Particular preference is given in turn to sulfosuccinates whose fatty alcohol radicals derive from ethoxylated fatty alcohols with narrow homolog distribution. It is likewise also possible to use alk(en)ylsuccinic acid with preferably 8 to 18 carbon atoms in the alk(en)yl chain or salts thereof.

Further suitable anionic surfactants are alkyl carboxylates, for example the sodium salts of saturated or unsaturated fatty acids, where the alkyl radical of the alkyl carboxylate is preferably linear.

In the context of the present invention, the activator is preferably selected from fatty alcohol alkoxylates, alkyl glycosides, alkyl carboxylates, alkylbenzenesulfonates, secondary alkanesulfonates and fatty alcohol sulfates, more preferably selected from fatty alcohol alkoxylates. One example of a preferred fatty alcohol alkoxylate is $C_6$-$C_{17}$(secondary)-poly(3-6)ethoxylate.

It is additionally preferred in the context of the present invention to use an activator which has a (relatively) high HLB (hydrophilic-lipophilic balance) value. The activator preferably has an HLB value of 7 to 18, more preferably of 8 to 15 and especially preferably of 9 to 13.

Activators with a high HLB value are preferably i) fatty alcohol alkoxylates formed from secondary alcohols or mixtures of alcohols having 12 to 18 carbon atoms and ethylene oxide or propylene oxide, and ii) alkyl glycosides formed from sucrose and $C_8$ to $C_{22}$ fatty alcohols. Examples of such activators are the commercially available Synperonic 87K from Croda GmbH, Herrenpfad-Süd 33, 41334 Nettetal, Germany; Croduret 40 or other ethoxylated hydrogenated castor oils (*ricinus* oils) such as Etocas 40 or Crodesta F110, all from Croda.

In a further embodiment of the present invention, it is preferred to use a mixture of at least two activators, at least one activator having a high HLB value and at least one activator a low HLB value. The activator with a high HLB value preferably has a HLB value of >12 to 20, and the activator with a low HLB value preferably has an HLB value of 1 to 12. In this embodiment, the activator with a high HLB value and the activator with a low HLB value may be present in any desired ratios known to those skilled in the art. Preferably, in the mixture, 20 to 50% by weight of activator with high HLB value and 50 to 80% by weight of activator with low HLB value are used. Additionally preferably, this ratio of activator with high HLB value to activator with low HLB value is adjusted such that the overall HLB value is 7 to 18, more preferably 8 to 15 and especially preferably 9 to 13.

In these mixtures of at least two activators, the activators with a high HLB value used are preferably alkyl glycosides or polyalkyl glycosides or polyalkyl oligoethylene oxide glycoside based on sucrose or sorbitan and $C_8$ to $C_{22}$ fatty alcohols such as polyethylene glycol sorbitan monostearate or polyoxyethylene sorbitan monostearate. Examples of such activators are the commercially available Crillet 1, Crillet 3 or Crodesta F160, all obtainable from Croda. The activators used with a low HLB value are preferably alkyl glycosides formed from sucrose or sorbitan and $C_8$ to $C_{22}$ fatty alcohols or fatty acids, such as sorbitan laurate or sorbitan stearate. Examples of such activators are the commercially available Crill 1, Crill 3 or Crodesta F10 from Croda.

According to the invention, the ratio of activator to the cationic polymer is >10:100 [% by weight/% by weight], preferably 10.5 to 50:100 [% by weight/% by weight], more preferably 11.5 to 20:100 [% by weight/% by weight].

In the inventive thickeners, further components may be present in addition to the cationic polymer and the activator. Suitable further components are defined in detail in the text which follows in the context of the preparation of the thickener and of the cationic polymer. Suitable further components may, for example, be oils and solvents.

In the inventive thickener, the cationic polymer may be present dispersed in the oil phase, preferably as an inverse dispersion, water-in-oil dispersion, or as a dispersed anhydrous cationic polymer in oil.

The present invention further provides a process for preparing the inventive thickeners. Thickener preparation processes as such and processes for preparing a polymer are known to those skilled in the art. The polymer is preferably obtained by an emulsion polymerization, especially by an inverse emulsion polymerization. The polymer is preferably first prepared and, after the polymerization, preferably by inverse emulsion polymerization, the activator is added to obtain the thickener.

The cationic polymer is preparable in various ways, preferably by emulsion polymerization, especially by inverse emulsion polymerization. Inverse emulsion polymerization is understood by the person skilled in the art generally to mean polymerization processes according to the following definition: the hydrophilic monomers are dispersed in a hydrophobic oil phase. The polymerization is effected directly in this hydrophilic monomer particle by addition of initiator.

In addition, it is preferred that, after the inverse emulsion polymerization and before the addition of activator, at least a portion of water and at least a portion of the low-boiling constituents of the oil phase are distilled off, especially by means of LDP technology (Liquid Dispersion Polymer Technology). LDP technology as such is known to those skilled in the art; it is described, for example, in WO 2005/097834.

The information which follows, unless stated otherwise, applies to all kinds of emulsion polymerization, for example to emulsion polymerization in water, which then constitutes the continuous phase, and especially also to inverse emulsion polymerization in which the hydrophobic oil phase constitutes the continuous phase. A suitable polymerization initiator is used for the polymerization. Redox initiators and/or thermally activatable free-radical polymerization initiators are preferred.

Suitable thermally activatable free-radical initiators or the oxidative component of the redox initiator pair are in particular those of the peroxy and azo type. These include hydrogen peroxide, peracetic acid, t-butyl hydroperoxide, di-t-butyl peroxide, dibenzoyl peroxide, benzoyl hydroperoxide, 2,4-dichlorobenzoyl peroxide, 2,5-dimethyl-2,5-bis(hydroperoxy)hexane, perbenzoic acid, t-butyl peroxypivalate, t-butyl peracetate, dilauroyl peroxide, dicapryloyl peroxide, distearoyl peroxide, dibenzoyl peroxide, diisopropyl peroxydicarbonate, didecyl peroxydicarbonate, dieicosyl peroxydicarbonate, di-t-butyl perbenzoate, azobisisobutyronitrile, 2,2'-azobis-2,4-dimethylvaleronitrile, ammonium persulfate, potassium persulfate, sodium persulfate and sodium perphosphate.

The persulfates (peroxodisulfates), especially sodium persulfate, are most preferred. In the performance of the emulsion polymerization, the initiator is used in a sufficient amount to initiate the polymerization reaction. The initiator is typically used in an amount of about 0.01 to 3% by weight, based on the total weight of the monomers used. The amount of initiator is preferably about 0.05 to 2% by weight and especially 0.1 to 1% by weight, based on the total weight of the monomers used.

The emulsion polymerization is effected typically at 0° C. to 100° C. It can be performed either as a batch process or in the form of a feed process. In the feed method, at least a portion of the polymerization initiator and optionally a portion of the monomers are initially charged and heated to polymerization temperature, and then the rest of the polymerization mixture is supplied, typically over several separate feeds, one or more of which comprise the monomers in pure or emulsified form, continuously or stepwise while maintaining the polymerization. Preference is given to supplying the monomer in the form of a monomer emulsion. In parallel to the monomer supply, further polymerization initiator can be metered in.

In preferred embodiments, the entire amount of initiator is initially charged, i.e. there is no further metering of initiator parallel to the monomer feed.

In a preferred embodiment, the thermally activatable free-radical polymerization initiator is therefore initially charged completely and the monomer mixture, preferably in the form of a monomer emulsion, is fed in. Before the feeding of the monomer mixture is started, the initial charge is brought to the activation temperature of the thermally activatable free-radical polymerization initiator or a higher temperature. The activation temperature is considered to be the temperature at which at least half of the initiator has decomposed after one hour.

In another preferred preparation method, the cationic polymer is obtained by polymerization of a monomer mixture in the presence of a redox initiator system. A redox initiator system comprises at least one oxidizing agent component and at least one reducing agent component, in which case heavy metal ions are preferably additionally present as a catalyst in the reaction medium, for example salts of cerium, manganese or iron(II).

Suitable oxidizing agent components are, for example, peroxides and/or hydroperoxides such as hydrogen peroxide, tert-butyl hydroperoxide, cumene hydroperoxide, pinane hydroperoxide, diisopropylphenyl hydroperoxide, dicyclohexyl percarbonate, dibenzoyl peroxide, dilauroyl peroxide and diacetyl peroxide. Hydrogen peroxide and tert-butyl hydroperoxide are preferred.

Suitable reducing agent components are alkali metal sulfites, alkali metal dithionites, alkali metal hyposulfites, sodium hydrogensulfite, Rongalit C (sodium formaldehydesulfoxylate), mono- and dihydroxyacetone, sugars (e.g. glucose or dextrose), ascorbic acid and salts thereof, acetone bisulfite adduct and/or an alkali metal salt of hydroxymethanesufinic acid. Sodium hydrogensulfite or sodium metabisulfite is preferred.

Suitable reducing agent components or catalysts are also iron(II) salts, for example iron(II) sulfate, tin(II) salts, for example tin(II) chloride, titanium(III) salts such as titanium (III) sulfate.

The amounts of oxidizing agent used are 0.001 to 5.0% by weight, preferably from 0.005 to 1.0% by weight and more preferably from 0.01 to 0.5% by weight, based on the total weight of the monomers used. Reducing agents are used in amounts of 0.001 to 2.0% by weight, preferably of 0.005 to 1.0% by weight and more preferably of 0.01 to 0.5% by weight, based on the total weight of the monomers used.

A particularly preferred redox initiator system is the sodium peroxodisulfate/sodium hydrogensulfite system, for example 0.001 to 5.0% by weight of sodium peroxodisulfate and 0.001 to 2.0% by weight of sodium hydrogensulfite, especially 0.005 to 1.0% by weight of sodium peroxodisulfate and 0.005 to 1.0% by weight of sodium hydrogensulfite, more preferably 0.01 to 0.5% by weight of sodium peroxodisulfate and 0.01 to 0.5% by weight of sodium hydrogensulfite.

A further particularly preferred redox initiator system is the t-butyl hydroperoxide/hydrogen peroxide/ascorbic acid system, for example 0.001 to 5.0% by weight of t-butyl hydroperoxide. 0.001 to 5.0% by weight of hydrogen peroxide and 0.001 to 2.0% by weight of ascorbic acid, especially 0.005 to 1.0% by weight of t-butyl hydroperoxide, 0.005 to 1.0% by weight of hydrogen peroxide and 0.005 to 1.0% by weight of ascorbic acid, more preferably 0.01 to 0.5% by weight of t-butyl hydroperoxide, 0.01 to 0.5% by weight of hydrogen peroxide and 0.01 to 0.5% by weight of ascorbic acid.

The cationic polymer is preferably prepared by inverse emulsion polymerization, by first separately preparing an aqueous phase of the water-soluble components and an oil phase. Thereafter, the two phases are mixed with one another to obtain a water-in-oil dispersion. The mixture is polymerized by adding a redox initiator system; optionally, another, thermal initiator can subsequently be added or, if already present, thermally activated.

The aqueous phase comprises, for example, a chain transfer agent, a crosslinker, a cationic monomer and optionally an uncharged monomer, and also the associative monomer, and optionally further components. Suitable further components are, for example, complexing agents for salts such as pentasodium diethylenetriaminepentaacetic acid, or compounds which can be used to adjust the pH, such as citric acid. In addition, an anionic monomer may optionally be present in the aqueous phase.

The oil phase preferably comprises an emulsifier, a stabilizer, a high-boiling oil, a low-boiling oil and/or optionally the associative monomer. In addition, the oil phase may optionally comprise a nonionic monomer.

Emulsifiers, stabilizers, low-boiling oils and high-boiling oils as such are known to those skilled in the art. These compounds can be used individually or in the form of mixtures.

Typical emulsifiers are anionic emulsifiers, for example sodium laurylsulfate, sodium tridecyl ether sulfates, dioctylsulfosuccinate sodium salt and sodium salts of alkylaryl polyether sulfonates; and nonionic emulsifiers, for example alkylaryl polyether alcohols and ethylene oxide-propylene oxide copolymers. Sorbitan trioleate is likewise suitable as an emulsifier.

Preferred emulsifiers have the following general formula:

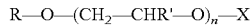

$$R-O-(CH_2-CHR'-O)_n-X$$

in which R is $C_6$-$C_{30}$-alkyl,
R' is hydrogen or methyl,
X is hydrogen or $SO_3M$,
M is hydrogen or one alkali metal, and
n is an integer from 2 to 100.

Suitable stabilizers are described, for example, in EP-A 172 025 or EP-A 172 724. Preferred stabilizers are copolymers of stearyl methacrylate and methacrylic acid.

Suitable high-boiling oils are, for example, 2-ethylhexyl stearate and hydroheated heavy naphtha, and suitable low-boiling oils are, for example, dearomatized aliphatic hydrocarbons or mineral oils of low viscosity.

In a preferred embodiment of the present invention, component b) (at least one ethylenically unsaturated associative monomer) is added to the oil phase in the inverse emulsion polymerization.

In the inverse emulsion polymerization, the temperature can be kept constant or else it can rise. The rise in the temperature can be performed continuously or in stages. For example, the temperature can rise by 0.2 to 10° C. per minute during the polymerization, preferably from 1 to 3° C. per minute. The temperature rise is controlled by the rate of initiator addition. The starting temperature value may be 0 to 30° C. preferably 10 to 20° C.

In another embodiment of the present invention, the temperature in the inverse emulsion polymerization is kept constant (cold method); the temperature is 0 to 30° C., preferably 10 to 20° C. In a further embodiment of the present invention, the temperature is kept constant within a higher temperature range (hot method). The temperature in the polymerization is 40 to 150° C., preferably 70 to 120° C.

In a particularly preferred embodiment of the present invention, the temperature is kept constant during the inverse emulsion polymerization, the temperature being at least 40° C., preferably 50 to 90° C.

If, in the context of the present invention, the temperature is kept constant in a polymerization, especially in an inverse emulsion polymerization, this means that the temperature is kept at a constant value from the start of the polymerization. Variations of +/−5° C., preferably +/−2° C. and especially +/−1° C. during the polymerization process are considered to be a constant temperature (based on the desired constant temperature value). The temperature is kept constant until the polymerization has ended, which is preferably the case after a conversion of more than 90% of the monomers used, more preferably more than 95% by weight and especially preferably at full conversion (100% by weight). The temperature can be kept constant by removing the heat of reaction which arises by cooling. The start of the polymerization is normally the addition of the polymerization initiator, preferably the addition of a redox initiator system. Normally, the system is first heated to the desired temperature and a constant temperature is awaited while stirring. Subsequently, the polymerization initiator is added, as a result of which the polymerization process commences. In one embodiment of the present invention, the temperature is kept constant at a value above the melting point of the associative monomer used.

The present invention further provides surfactant-containing acidic formulations comprising at least one inventive thickener according to the above definitions. The pH of the formulation is 1 to <7.

The present invention further provides surfactant-containing alkaline formulations comprising at least one inventive thickener according to the above definitions. The pH of the formulation is 7 to 13.

The inventive surfactant-containing acidic or alkaline formulations may comprise further ingredients known to those skilled in the art. Suitable ingredients comprise one or more substances from the group of the builders, bleaches, bleach activators, enzymes, electrolytes, nonaqueous solvents, pH modifiers, fragrances, perfume carriers, fluorescers, dyes, hydrotropes, foam inhibitors, silicone oils, antiredeposition agents, optical brighteners, graying inhibitors, antishrink agents, anticrease agents, dye transfer inhibitors, active antimicrobial ingredients, germicides, fungicides, antioxidants, corrosion inhibitors, antistats, ironing aids, hydrophobizing and impregnating agents, swelling and antislip agents, and UV absorbers.

In one embodiment of the present invention, the surfactant-containing formulations, especially surfactant-containing acidic formulations, comprise less than 1% by weight of thickener (based on the overall formulation), the cationic polymer of the thickener being obtained by inverse emulsion polymerization at constant temperature. Preferably, the formulations comprise 0.1 to <1% by weight of thickener.

The present invention further provides for the use of an inventive surfactant-containing acidic formulation in hair cosmetics, in hair styling, as a shampoo, as a softener, as a conditioner, as a skin cream, as a shower gel, as a fabric softener for laundry, or as an acidic detergent, preferably for toilets or baths.

The present invention further provides for the use of a surfactant-containing alkaline formulation as a liquid washing composition or as a machine or manual dishwashing detergent.

The present invention further provides for the use of the inventive thickener as a viscosity modifier, for optimization of shear dilution, as a thickening agent, for stabilization of suspended constituents having a size in the range from nanometers to millimeters and/or in surfactant-containing acidic or alkaline formulations.

In the description including the examples, the following abbreviations are used:

Monomers
ACM acrylamide
AA acrylic acid
MAA methacrylic acid
NaAc sodium acrylate
TMAEC 2-trimethylammoniumethyl acrylate chloride
TMAEMC 2-trimethylammoniumethyl methacrylate chloride
BEM behenyl-25 methacrylate
MBA methylene-bis-acrylamide (crosslinker)
TAAC tetraallyl-ammonium chloride (crosslinker)
NaHP sodium hypophosphite (chain transfer agent)
C16EO25MAc $C_{16}$-$C_{18}$-fatty alcohol-(ethylene glycol)$_{25}$ ether methacrylate
Others
pphm parts per hundred parts of monomers (based on components a) and b))

The invention is illustrated hereinafter by the examples.

EXAMPLES

Comparative Example C1

Synthesis of a thickener/polymer proceeding from cationic monomers without associative monomer, but with crosslinker and chain transfer agent and rising polymerization temperature.

An aqueous phase of water-soluble components is prepared by mixing the following components:
1.23 g (0.5 pphm) of citric acid 1-hydrate,
43.73 g (17.85 pphm) of water,
0.7 g (0.29 pphm) of pentasodium diethylenetriaminepentaacetic acid,
14.78 g (0.06 pphm) of methylenebisacrylamide (1% in water),
4.9 g (0.02 pphm) of tetraallylammonium chloride (1% in water),
8 g (0.16 pphm) of sodium hypophosphite (5% in water), and
326.66 g (100 pphm) of 2-trimethylammoniumethyl methacrylate chloride (quaternized dimethylaminoethyl methacrylate) (TMAEMC, 75% in water).

An oil phase is prepared by mixing the following components:
8 g (2.45 pphm) of sorbitan trioleate (75% in dearomatized aliphatic hydrocarbon [Exxsol D40]),
67.83 g (5.23 pphm) of a polymeric stabilizer: stearyl methacrylate-methacrylic acid copolymer (19% in dearomatized aliphatic hydrocarbon [Exxsol D40]),
151.29 g (61.75 pphm) of 2-ethylhexyl stearate (Crodamol OS) and
60.17 g (24.56 pphm) of dearomatized aliphatic hydrocarbon [Exxsol D40].

The two phases are mixed in a ratio of 58.2 parts of aqueous phase to 41.8 parts of oil phase with high shear, and a water-in-oil emulsion is thus prepared. The water-in-oil emulsion which forms is introduced into a reactor equipped with nitrogen spray line, stirrer and thermometer. The emulsion is purged with nitrogen, which removes the oxygen, and is then cooled to 20° C.

The polymerization is achieved by adding a redox pair composed of
10 g (0.04 pphm) of sodium metabisulfite (1% in dearomatized aliphatic hydrocarbon [Exxsol D40]) and
10 g (0.04 pphm) of tert-butyl hydroperoxide (1% in dearomatized aliphatic hydrocarbon [Exxsol D40]).

The redox pair is added stepwise such that there is a temperature increase of 2° C./min. Once the isotherm has been attained, a free radical initiator (2,2'-azobis(2-methylbutyronitrile), CAS: 13472-08-7) is added in two steps (the 2nd step after 45 min) and the emulsion is kept at 85° C. for 75 minutes.

By means of vacuum distillation, water and low-boiling constituents of the oil phase (Exxsol D40) are removed.

2-ethylhexyl stearate (Crodamol OS) is added to the vacuum-distilled product, which achieves a solids content of 53.5%. Thereafter, 7% (based on the total proportion by mass of this product) of a fatty alcohol alkoxylate [alcohol C6-C17 (secondary) poly(3-6)ethoxylate: 97% secondary alcohol ethoxylate+3% poly(ethylene oxide)], known as Tergitol™ 15-S-7 (CAS No. 84133-50-6), are added to produce a thickener (dispersion) with 50% polymer solids content. The ratio of activator to cationic polymer is thus 14.0:100 [% by weight/% by weight].

Comparative Example C2

Synthesis of a thickener/polymer proceeding from cationic monomers without associative monomer and chain transfer agent, but with crosslinker and rising polymerization temperature.

The synthesis is performed as in C1, but with the difference that no sodium hypophosphite (5% in water) and no tetraallylammonium chloride (1% in water) are added, and the amount of water is increased by 12.9 g of water. The ratio of activator to cationic polymer is 14.0:100 [% by weight/% by weight].

Comparative Example C3

Synthesis of a thickener/polymer proceeding from cationic monomers without associative monomer, chain transfer agent and crosslinker at constant polymerization temperature.

An aqueous phase of water-soluble components is prepared by mixing the following components:
1.88 g (0.5 pphm) of citric acid 1-hydrate,
109.85 g (29.32 pphm) of water,
1.07 g (0.29 pphm) of pentasodium diethylenetriaminepentaacetic acid,
500.00 g (100 pphm) of 2-trimethylammoniumethyl methacrylate chloride (quaternized dimethylaminoethyl methacrylate) (TMAEMC 75% in water).

An oil phase is prepared by mixing the following components:
12.24 g (2.45 pphm) of sorbitan trioleate (75% in dearomatized aliphatic hydrocarbon [Exxsol D40]),
103.83 g (5.22 pphm) of a polymeric stabilizer: stearyl methacrylate-methacrylic acid copolymer (19% in dearomatized aliphatic hydrocarbon [Exxsol D40]),
231.57 g (61.75 pphm) of 2-ethylhexyl stearate (Crodamol OS), and
92.10 g (24.56 pphm) of dearomatized aliphatic hydrocarbon [Exxsol D40].

The two phases are mixed in a ratio of 58.2 parts of aqueous phase to 41.8 parts of oil phase with high shear to produce a water-in-oil emulsion. The water-in-oil emulsion which forms is introduced into a reactor equipped with nitrogen spray line, stirrer and thermometer. The emulsion is purged with nitrogen, which removes the oxygen.

The polymerization is achieved by adding a redox pair consisting of
13 g (0.05 pphm) of sodium metabisulfite (1% in demineralized water) and
13 g (0.05 pphm) of tert-butyl hydroperoxide (1% in demineralized water).

The rate for the addition of the redox pair is 13 g in 2 hours, the temperature being kept constant at 50° C. Thereafter, a free radical initiator (2,2'-azobis(2-methylbutyronitrile), CAS: 13472-08-7) is added in two steps (the 2nd step after 45 min) and the emulsion is kept at 85° C. for 75 minutes.

By means of vacuum distillation, water and low-boiling constituents of the oil phase (Exxsol D40) are removed.

2-ethylhexyl stearate (Crodamol OS) is added to the vacuum-distilled product to achieve a solids content of 53.5%.

Thereafter, 7% (based on the total proportion by mass of this product) of a fatty alcohol alkoxylate [alcohol C6-C17 (secondary) poly(3-6)ethoxylate: 97% secondary alcohol ethoxylate+3% poly(ethylene oxide)], known as Tergitol™ 15-S-7 (CAS No. 84133-50-6), is added to prepare a thickener (dispersion) with polymer solids content 50%. The ratio of activator to cationic polymer is thus 14.0:100 [% by weight/% by weight].

Comparative Examples C4-C5

As C1, but with changes according to Table 1:

TABLE 1

| Examples | TMAE MC (pphm) | MBA | TAAC | NaHP | Comment |
|---|---|---|---|---|---|
| C4 | 50 | 0.0025 | 0.0025 | 0.001 | 50 pphm of acrylamide |
| C5 | 100 | 0.18 | 0.06 | 0.02 | |

The ratio of activator to cationic polymer in comparative examples C4 and C5 is in each case 14.0:100 [% by weight/% by weight].

Example 1

Thickeners/polymers proceeding from cationic monomers with associative monomer:

The examples which follow according to Table 2 are produced like comparative example C3 with incorporation of the specified changes in the monomer composition and in the temperature regime. The associative monomer C16EO25MAc is introduced into the oil phase. The commercial product Plex 6954 O is used, which comprises 60% by weight of associative monomer and, as solvents, water and MAA in a ratio of approx. 1:1. The weight data in Table 2 are based on the amount of associative monomer without solvent. The ratio of activator to cationic polymer in all examples according to Table 1 is in each case 14.0:100 [% by weight/% by weight]; unless stated otherwise, the particular thickeners (dispersion) have polymer solids content 50%.

TABLE 2

| Examples | C16EO25 MAc (pphm) | TMAEMC (pphm) | MBA | TAAC | NaHP | Comment |
|---|---|---|---|---|---|---|
| 1.1 | 0.19 | 99.75 | — | — | — | |
| 1.2 | 0.19 | 99.75 | — | — | — | Temperature regime as C1; polymer solids content 30%; amount of activator adjusted correspondingly |
| 1.3 | 0.19 | 99.75 | — | — | — | Temperature regime as C1, but +1° C./min |
| 1.4 | 0.19 | 99.75 | — | — | 0.16 | Temperature regime as C1 |
| 1.5 | 0.19 | 99.75 | 0.06 | 0.02 | 0.05 | |
| 1.6 | 0.19 | 99.75 | — | — | — | Temperature regime as C1 |
| 1.7 | 0.38 | 74.50 | | | | 25 pphm of acrylamide |
| 1.9 | 0.76 | 99.00 | | | | |
| 1.10 | 0.38 | 49.5 | | | | 50 pphm of acrylamide |

General Test Methods

Unless stated otherwise, the following general test methods are used in the examples which follow:

Determination of Viscosity

With reference to the methods according to DIN 51550, DIN 53018, DIN 53019, the Brookfield model DV II viscometer is used, unless stated otherwise within the following tables, at the speed of 10 revolutions per minute with the specified spindle no. 2 to measure the viscosities reported in mPas.

Determination of Shear Dilution

Measurement is effected in an ASC (automatic sample changer) rotary rheometer from Antonpaar, with the CC27 cylinder geometry, a radius of the measurement body of 13.33 mm and a radius of the measurement cup of 14.46 mm. The measurement temperature is 23° C. The samples are measured at steady-state shear, beginning at small shear, increasing (0.01 s$^{-1}$-1000 s$^{-1}$) and decreasing again (1000 s$^{-1}$-0.01 s$^{-1}$).

Example 2

Thickeners/polymers proceeding from cationic monomers with associative monomer, and influence of the amount of activator on the thickening rate in aqueous formulations:

Examples 2.1 to 2.5 listed in Table 3 are prepared in accordance with example 1.5 from Table 2, except that the amount of activator added after the distillation is varied according to the activator concentration (A %) in the thickener specified in Table 3 (all figures in % by weight based on the amount of cationic polymer in the thickener). All thickeners thus prepared (dispersion) have polymer solids content 50%. The thickeners are subsequently added to the water while stirring. These resulting aqueous formulations comprise 1% by weight of thickener to 99% by weight of water, i.e. 0.5% by weight of polymer to 99.5% by weight of water. C means comparative example.

TABLE 3

| Examples | A % | Thickening rate (Brookfield visc. mPa * s) of the aqueous formulations | | | | | | | |
|---|---|---|---|---|---|---|---|---|---|
| | | 1 min. | 2 min. | 3 min. | 5 min. | 10 min. | 20 min. | 40 min. | 1 H |
| 2.1 (C) | 2.0 | 20 | 20 | 24 | 28 | 36 | 248 | 4800 | 7370 |
| 2.2 (C) | 6.0 | 20 | 24 | 28 | 128 | 3640 | 8300 | 9630 | 10600 |
| 2.3 | 14.0 | 72 | 740 | 2600 | 6200 | 9100 | 11120 | 12220 | 12440 |
| 2.4 | 20.0 | 9100 | 10000 | 11060 | 11880 | 12540 | 12540 | 12780 | 12780 |
| 2.5 | 34.0 | 13280 | 13200 | 13140 | 13060 | 12920 | 12900 | 12800 | 12800 |

Aqueous formulations based on thickeners with 6% activator (ex. 2.2) have only attained a viscosity in the lower three-digit mPas range after 5 minutes. In contrast, the corresponding value for example 2.3 (14.0% activator) is already in the middle four-digit mPas range after 5 minutes.

Example 3

Use of the thickeners/polymers in standard formulations of fabric softeners
W1: Preparation of a Di(Hydrogenated Tallow)Dimethylammonium Chloride (DHTDMAC) Fabric Softener (Active Content 4%)
To 1890 g of deionized preheated water are slowly added, while stirring, 111 g of DHTDMAC (Arquad® 2HT-75) melted at 50° C. The dispersion is stirred and heated to 50° C. while stirring constantly for 15 minutes. The mixture is cooled to 30° C. while stirring. The pH is adjusted to 4.0 by adding citric acid solution. The fabric softener is homogenized by stirring.
LV Brookfield Viscosity (22° C., 30 rpm)=90 mPa·s.
W3: Preparation of a Methyltris(Hydroxyethyl)Ammonium Ditallow Fatty Acid Ester Methosulfate, Partly Hydrogenated, Fabric Softener (Active Content 5.5%)
The fabric softener has a pH of 2.7 and comprises 5.5% by weight of methyltris(hydroxyethyl)ammonium ditallow fatty acid ester methosulfate (partly hydrogenated) and 94.5% by weight of demineralized water.
Addition of the Thickener to Fabric Softener Formulations W1 to W3:
The thickeners according to example 1 (Table 2) and comparative examples are added gradually at room temperature to the particular fabric softener formulation and stirred until the formulation has homogenized.
The Brookfield viscosity is measured one day after the preparation. The results are compiled in Table 4.

In addition to the high thickening performance, the relative percentage shear dilution in the inventive thickeners is also much greater than in the comparative examples without associative monomer (like 3.1, 3.3 and 3.4).

Example 4

Use of the thickeners/polymers in standard formulations of acidic detergents
R1: Preparation of an Acidic Detergent of the Following Composition:
pH=5.3;
12 g of $C_{13}$-$C_{15}$ oxo alcohol ethoxylate with 8 EO
4 g of $C_{13}$-$C_{15}$ oxo alcohol ethoxylate with 5 EO
2.5 g of ethylhexanol ethoxylate
81.5 g of demineralized water
R2: Preparation of an Acidic Detergent of the Following Composition:
pH=1.8;
10.3 g of $C_{13}$-$C_{15}$ oxo alcohol ethoxylate with 8 EO
3.4 g of $C_{13}$-$C_{15}$ oxo alcohol ethoxylate with 5 EO
2.2 g of ethylhexanol alkoxylate
8.6 g of citric acid
75.5 g of demineralized water
The particular thickeners are added to these standard formulations as described above in example 3. The Brookfield viscosity is measured one day after the preparation. The results are compiled in Table 5.

TABLE 4

Thickener performance and shear dilution in fabric softeners
Rheology of fabric softeners comprising thickeners/polymers proceeding from cationic monomers:

| Example No. | Formulation | Thickener No. | Thickener concentration (%) | Viscosity at 0.1 s$^{-1}$ (mPa * s) | Viscosity at 10 s$^{-1}$ (mPa * s) | Viscosity at 100 s$^{-1}$ (mPa * s) | Viscosity at 1000 s$^{-1}$ (mPa * s) |
|---|---|---|---|---|---|---|---|
| 3.1 (C) | W3 | V1 | 0.5 | 27992 | 833 | 221 | 63 |
| 3.2 | W3 | 1.5 | 0.5 | 65986 | 1599 | 377 | 67 |
| 3.3 (C) | W3 | V1 | 1.0 | 47051 | 1441 | 352 | 106 |
| 3.4 (C) | W3 | V3 | 1.0 | 11062 | 901 | 213 | 56 |
| 3.5 | W3 | 1.7 | 1.0 | 58440 | 2579 | 470 | 104 |

TABLE 5

Thickener performance in acidic detergents
Rheology of acidic detergents comprising thickeners/polymers proceeding from cationic monomers:

| Example No. | Formulation | Thickener No. | Thickener concentration (%) | Viscosity at 0.1 s$^{-1}$ (mPa * s) | Viscosity at 10 s$^{-1}$ (mPa * s) | Viscosity at 100 s$^{-1}$ (mPa * s) |
|---|---|---|---|---|---|---|
| 4.1 (C) | R1 | V1 | 1 | 16408 | 1850 | 618 |
| 4.2 | R1 | 1.5 | 1 | 140080 | 6100 | 1425 |
| 4.3 (C) | R1 | V3 | 1 | 4620 | 810 | 232 |
| 4.4 | R1 | 1.7 | 1 | 13124 | 1163 | 301 |
| 4.5 (C) | R2 | VI | 1 | 7550 | 962 | 350 |
| 4.6 (C) | R2 | V3 | 1 | 927 | 405 | 140 |
| 4.7 | R2 | 1.5 | 1 | 20918 | 1775 | 593 |

In addition to the high thickening performance, the relative percentage shear dilution in the inventive thickeners is also much greater than in the comparative examples without associative monomer (like 4.1).

Example 5

Use of the thickeners/polymers in aqueous formulations
The aqueous formulations are prepared as described above in example 2. The Brookfield viscosity is measured one day after the preparation. The results are compiled in Table 6.

TABLE 6

Rheology of thickeners/polymers proceeding from cationic monomers in water

| Example No. | Formulation | Thickener No. | Thickener concentration (%) | Brookfield spindle 3 (1 rpm)/ mPas | Brookfield spindle 3 (10 rpm)/ mPas | Brookfield spindle 3 (50 rpm)/ mPas | Brookfield spindle 3 (100 rpm)/ mPas |
|---|---|---|---|---|---|---|---|
| 5.1 (C) | Water | V2 | 1 | 120 | 20 | 36 | 42 |
| 5.2 | Water | 1.2 | 1 | 480 | 300 | 182 | 145 |

Example 6

In Tables 7 and 8 below, the storage stability of the inventive thickeners (according to example 1) and corresponding fabric softener formulations (according to example 3) is examined. It is found that the inventive thickeners are much more stable.

TABLE 7

Storage stability of thickeners/polymers proceeding from cationic monomers:

| Example | Thickener No. | Immediate precipitate | Precipitate after 4 days at 40° C. | Precipitate after 3 weeks at 40° C. | Precipitate after 10 weeks at 40° C. |
|---|---|---|---|---|---|
| 6.1 (C) | V1 | none | distinct, redispersible | distinct, redispersible | distinct, redispersible |
| 6.2 | 1.1 | none | none | none | none |
| 6.3 | 1.2 | none | none | none | none |
| 6.4 | 1.3 | none | none | none | none |
| 6.5 | 1.4 | none | none | none | none |
| 6.6 | 1.5 | none | none | none | none |

TABLE 8

Storage stability of fabric softeners W1 comprising thickeners/polymers proceeding from cationic monomers:

| Example | Cationic LDP dispersion | Immediate precipitate | Precipitate after 4 days at 40° C. | Precipitate after 3 weeks at 40° C. | Precipitate after 10 weeks at 40° C. |
|---|---|---|---|---|---|
| 6.7 (C) | V1 | none | distinct, redispersible | distinct, redispersible | distinct, redispersible |
| 6.8 | 1.1 | none | none | none | none |
| 6.9 | 1.2 | none | none | none | none |
| 6.10 | 1.3 | none | none | none | none |
| 6.11 | 1.4 | none | none | none | none |
| 6.12 | 1.5 | none | none | none | none |

Example 7

Thickeners/polymers proceeding from cationic monomers with associative monomer, and influence of the amount of activator on the thickening rate in fabric softener formulations:
Examples 2.1 to 2.5 in aqueous formulation described in Table 3 are performed analogously according to example 3 in fabric softener formulations with fabric softeners (W3)

according to Table 9 as examples 7.1-7.5: again, the activator concentration (A %) in the thickener is varied, and the amount of activator added after the distillation is varied in accordance with the activator concentration (A %) in the thickener specified in Table 9 (all figures in % by weight are based on the amount of cationic polymer in the thickener). All thickeners thus prepared (dispersion) have polymer solids content 50%. These thickeners are added to the fabric softener W3 while stirring. The thickened fabric softener formulations obtained comprise 1% by weight of thickener to 99% by weight of fabric softener W3, i.e. 0.5% by weight of polymer to 99.5% by weight of fabric softener W3.

TABLE 9

| | | Thickening rate (Brookfield visc. mPa * s at 10 rpm) | | | | | | | | |
|---|---|---|---|---|---|---|---|---|---|---|
| Example | A % | 1 min. | 2 min. | 3 min. | 5 min. | 10 min. | 20 min. | 40 min. | 1 H | 3 H |
| 7.1 (C) | 3.0 | 152 | 244 | 368 | 644 | 1316 | 2376 | 3616 | 4930 | 9180 |
| 7.2 (C) | 6.0 | 248 | 492 | 784 | 1400 | 2468 | 3336 | 4520 | 5020 | 7560 |
| 7.3 | 14.0 | 1900 | 2900 | 3680 | 4650 | 5200 | 5420 | 5600 | 5750 | 6280 |
| 7.4 | 20.0 | 2700 | 3572 | 3996 | 4600 | 4690 | 4650 | 4880 | 4820 | 5400 |
| 7.5 | 34.0 | 5600 | 5560 | 5480 | 5340 | 5200 | 4810 | 4810 | 4810 | 5000 |

Fabric softeners based on thickeners with an activator content of more than 10% (ex. 7.3-7.5) have obtained about 75% of the final viscosity within 5 minutes. Below this limit, this value is attainable only after 40 minutes. The higher the activator concentration established, the more rapidly the final viscosity in the formulation is obtained.

Example 8

Influence of the amount of crosslinker on the solubility of the polymers present in the thickener (proceeding from cationic monomers):

The measurement of the soluble polymer components given in Table 10 is effected according to the method of P. Schuck ('Size-distribution analysis of macromolecules by sedimentation velocity ultracentrifugation and Lamm equation modeling', Biophysical Journal 78, (3) (2000), 1606-1619.).

TABLE 10

Determination of the solubility of the TMAEMC copolymers present in the thickener by means of an analytical ultracentrifuge (AUC)

| Examples | Polymer | Soluble TMAEMC copolymer in thickener (dispersion) (% based on overall polymer) |
|---|---|---|
| 8.1 (C) | V1 | 24 |
| 8.2 (C) | V5 | <1 |
| 8.3 | 1.6 | 100 |
| 8.4 | 1.9 | 100 |
| 8.5 (C) | V4 | 22 |
| 8.6 | 1.10 | 83 |

The TMAEMC copolymers which have been prepared with 800 pphm or more of crosslinker comprise less than 24% soluble components. The TMAEMC copolymers which have been prepared without crosslinker and in some cases with less than 1 pphm of associative monomers comprise more than 99% soluble components. Acrylamide as a comonomer in TMAEMC copolymers reduces the solubility of the copolymer.

The invention claimed is:
1. A thickener comprising
  i) at least one cationic polymer preparable by polymerization of
    a) at least one water-soluble ethylenically unsaturated monomer comprising at least one cationic monomer, optionally at least one anionic monomer or optionally at least one nonionic monomer,
    b) at least one ethylenically unsaturated associative monomer,
    c) optionally at least one crosslinker,
    d) optionally at least one chain transfer agent,
  ii) at least one activator,
where the ratio of activator to cationic polymer is 10.5:100 to 50:100 [% by weight/% by weight];
wherein the at least one cationic monomer according to component a) in the cationic polymer is selected from a compound of the formula (II)

$$R_1-\underset{H}{C}=\underset{R_2}{C}-\underset{\parallel}{\overset{O}{C}}-X-R_3-\underset{R_6}{\overset{R_4}{\underset{|}{N^+}}}-R_5 \quad Y^- \tag{II}$$

where
$R_1$ is H or $C_1$-$C_4$-alkyl,
$R_2$ is H or methyl,
$R_3$ is $C_1$-$C_4$-alkylene,
$R_4$, $R_5$ and $R_6$ are each independently H or $C_1$-$C_{30}$-alkyl,
X is —O— or —NH— and
Y is Cl; Br; I; hydrogensulfate or methosulfate;
wherein the nonionic monomer according to component a) in the cationic polymer is selected from N-vinylpyrrolidone, N-vinylimidazole or a compound of the formula (III)

$$R_7-\underset{H}{C}=\underset{R_8}{C}-\underset{\parallel}{\overset{O}{C}}-N\underset{R_{10}}{\overset{R_9}{\diagup}} \tag{III}$$

where
$R_7$ is H or $C_1$-$C_4$-alkyl,
$R_8$ is H or methyl, and
$R_9$ and $R_{10}$ are each independently H or $C_1$-$C_{30}$-alkyl;
wherein the at least one ethylenically unsaturated associative monomer according to component b) in the cationic polymer is selected from a compound of the formula (I)

$$R-O-(CH_2-CHR'-O)_n-CO-CR''=CH_2 \tag{I}$$

where
R is $C_6$-$C_{50}$-alkyl,
R' is H or $C_1$-$C_4$-alkyl,
R" is H or methyl,
n is an integer from 0 to 100;
wherein the crosslinker (component c)) in the cationic polymer is selected from divinylbenzene; tetraallylammonium chloride; allyl acrylates; allyl methacrylates; diacrylates and dimethacrylates of glycols or polyglycols; butadiene; 1,7-octadiene, allylacrylamides or allylmethacrylamides; bisacrylamidoacetic acid; N,N'-methylenebisacrylamide, or polyol polyallyl ethers; polyallyl sucrose or pentaerythritol triallyl ether;
wherein the chain transfer agent (component d) in the cationic polymer is selected from the group consisting of mercaptans, lactic acid, formic acid, isopropanol, hypophosphites, and combinations thereof; and
wherein the activator is selected from the group consisting of fatty alcohol alcoxylates, alkyl glycosides, alkyl carboxylates, alkylbenzenesulfonates, secondary alkanesulfonates, fatty alcohol sulfates, and combinations thereof.

2. The thickener according to claim 1, wherein component a) in the cationic polymer comprises 30 to 99.5% by weight of at least one cationic monomer and 0.5 to 70% by weight of at least one nonionic monomer.

3. The thickener according to claim 1, wherein, in the cationic monomer of the formula (II),
i) $R_1$ and $R_2$ are each H or
ii) $R_1$ is H and $R_2$ is $CH_3$.

4. The thickener according to claim 1, wherein the activator is selected from fatty alcohol alcoxylates.

5. The thickener according to claim 1, wherein a mixture of at least two activators is used, at least one activator having an HLB (hydrophilic-lipophilic balance) value of >12 to 20 and at least one activator an HLB value of 1 to 12.

6. The thickener according to claim 1, which is present in a dispersion comprising an oil phase, wherein the cationic polymer is present dispersed in the oil phase.

7. The thickener according to claim 6, wherein the dispersion is an inverse dispersion, water-in-oil dispersion, or a dispersed anhydrous cationic polymer in oil.

8. The thickener according to claim 1, wherein more than 25% by weight, based on the total weight of the cationic polymer, of the cationic polymer is soluble in water.

9. A process for preparing a thickener according to claim 1, which comprises obtaining the cationic polymer by an emulsion polymerization.

10. The process according to claim 9, wherein the cationic polymer is obtained by an inverse emulsion polymerization.

11. The process according to claim 10, wherein the inverse emulsion polymerization is followed and the activator addition is preceded by distillative removal of at least a portion of water and at least a portion of the low-boiling constituents of the oil phase.

12. The process according to claim 11, which is carried out by means of LDP (liquid dispersion polymer) technology.

13. The process according to claim 10, wherein component b) is added to the oil phase in the inverse emulsion polymerization.

14. The process according to claim 10, wherein the temperature is kept constant or rises during the inverse emulsion polymerization.

15. The process according to claim 10, wherein the temperature is kept constant during the inverse emulsion polymerization and is at least 40° C.

16. A surfactant-containing acidic formulation comprising at least one thickener according to claim 1, the pH of the formulation being 1 to <7.

17. The surfactant-containing acidic formulation according to claim 16 to be used in hair cosmetics, in hair styling, as a shampoo, as a softener, as a conditioner, as a skin cream, as a shower gel, as a fabric softener for laundry, or as an acidic detergent.

18. A surfactant-containing alkaline formulation comprising at least one thickener according to claim 1, the pH of the formulation being 7 to 13.

19. The surfactant-containing alkaline formulation according to claim 18 to be used as a liquid washing composition or as a machine or manual dishwashing detergent.

20. The thickener according to claim 1 to be used as a viscosity modifier, for optimization of shear dilution, as a thickening agent, for stabilization of suspended constituents having a size in the range from nanometers to millimeters or in surfactant-containing acidic or alkaline formulations.

21. The thickener according to claim 1, wherein the ratio of activator to cationic polymer is 11.5:100 to 50:100[% by weight/% by weight].

22. The thickener according to claim 1, wherein the ratio of activator to cationic polymer is 14.0:100 to 50:100 [% by weight/% by weight].

23. The thickener according to claim 1, wherein
in formula (II) $R_1$ is H;
in formula (I) R is $C_8$-$C_{30}$-alkyl, R' is H, and n is an integer from 3 to 50;
and wherein the activator is selected from fatty alcohol alcoxylates.

24. The thickener according to claim 1 wherein the crosslinker (component c)) in the cationic polymer is selected from the group consisting of methylene-bis-acrylamide and tetraallyl-ammonium chloride.

25. The thickener according to claim 17 wherein the crosslinker (component c)) in the cationic polymer is selected from the group consisting of methylene-bis-acrylamide and tetraallyl-ammonium chloride.

26. The thickener according to claim 1, wherein the chain transfer reagent is sodium hypophosphite.

27. The thickener according to claim 17, wherein the chain transfer reagent is sodium hypophosphite.

28. The surfactant-containing acidic formulation according to claim 17, wherein the ratio of activator to cationic polymer is 11.5:100 to 50:100[% by weight/% by weight].

29. The surfactant-containing acidic formulation according to claim 17, wherein the ratio of activator to cationic polymer is 14.0:100 to 50:100 [% by weight/% by weight].

* * * * *